United States Patent

Schmäh

Patent Number: 5,439,581
Date of Patent: Aug. 8, 1995

[54] SOLID ELECTROLYTE SENSOR

[75] Inventor: Martin Schmäh, Frankfurt, Germany

[73] Assignee: Mannesmann Aktiengesellschaft, Dusseldorf, Germany

[21] Appl. No.: 224,160

[22] Filed: Apr. 7, 1994

[30] Foreign Application Priority Data

Apr. 7, 1993 [DE] Germany .............. 43 11 985.9

[51] Int. Cl.⁶ ............................................ G01N 27/26
[52] U.S. Cl. ............................. 204/427; 204/425; 204/410; 204/412
[58] Field of Search .............. 204/421, 415, 424, 425, 204/426, 427, 406, 410, 412

[56] References Cited

U.S. PATENT DOCUMENTS 4,927,517  5/1990  Mizutani et al. ................ 204/425
4,988,428  1/1991  Iwakiri et al. ................... 204/406

FOREIGN PATENT DOCUMENTS 2736451  3/1978  Germany .
3730079  3/1988  Germany .

OTHER PUBLICATIONS

Rickert, Feste Ioneuleiter—Grundlagen und Anwendungen, Angew, Chem 90, 38–48 (1978).

Primary Examiner—John Niebling
Assistant Examiner—Bruce F. Bell
Attorney, Agent, or Firm—Cohen, Pontani, Lieberman, Pavane

[57] ABSTRACT

A solid electrolyte sensor device for determining gas concentrations in measurement gases, with a sensor formed by a solid electrolyte which is arranged between at least two electrodes. The electrodes are permeable to gas and at least one of the electrodes faces the measurement gas. An electrical device is also provided for detecting and processing concentration-dependent sensor output values. For the purpose of permanently preventing disruptive adsorption of measurement gas components on the sensor or on the corresponding sensor electrode, an adjustable oxygen source is arranged in the vicinity of the sensor electrode which faces the measurement gas so that oxygen or oxygen radicals can be introduced into the measurement gas via this oxygen source for the oxidation of the measurement gas.

7 Claims, 4 Drawing Sheets

SOLID ELECTROLYTE SENSOR

BACKGROUND OF THE INVENTION

1. Field of the Invention

The invention is directed to a solid electrolyte sensor device for measuring gas compositions, which device has a solid electrolyte arranged between at least two electrodes. The electrodes are gas permeable and at least one of the electrodes faces the measurement gas. The device also has an electrical device for detecting and processing concentration dependent sensor output values.

2. Description of the Prior Art

Solid electrolyte sensors of the type mentioned above, which are used to determine gas concentrations, are galvanic chains formed by a solid electrolyte and two or more electrodes. The solid electrolyte itself is a solid body which is conductive for at least one type of ion due to its imperfection. In this context, imperfection is understood to mean the divergence of a crystal lattice from the specific ideal orderly structure. At final temperatures, there may be unoccupied positions in a crystal lattice- so-called vacancies and additional interstitial atoms or ions in the intersticies, i.e. between the regular positions of the host lattice. Other imperfections may consist of foreign ions located, for example, on interstitial sites. The ion conductivity depends on the temperature and increases as the temperature increases. The basic use of such ion conductors as solid electrolyte sensors is known from the article "Solid Ion Conductors–Fundamentals and Applications" (Prof. Dr. Rickert), Applied Chemistry 90, 38 to 48 (1978). A very popular example of a solid electrolyte sensor is the so-called lambda probe for determining oxygen concentrations in motor vehicle exhaust, waste gases from furnace installations, and the like.

Solid electrolyte sensors are known for verifying or determining the concentration of other gas components such as chlorine, sulfur dioxide, carbon dioxide, nitric oxides, etc. In these solid electrolyte sensors, the solid electrolyte does not convert the gas component to be verified- as with zirconium dioxide and oxygen - but rather conducts ions which react with these gas components to form a chemical bond. In many applications, verification of the gas component by a solid electrolyte requires conversion of the gas component to be measured. This is true, for example, when measuring sulfur dioxide which must be converted to sulfur trioxide. Platinum or vanadium pentoxide catalysts are conventionally used for this purpose.

In general, the problem with known arrangements is that the measurement gas component can only be verified with difficulty, if at all, or that the measurement gas component overreacts chemically with the electrode material and is adsorbed on the measurement electrode. It is known to use the above-mentioned catalysts to prevent such interaction with the measurement electrode. However, these catalysts bring about a pure surface reaction with the measurement gas. This has the grave disadvantage that the catalytic efficiency is not constant and accordingly constant measurement conditions cannot be maintained along the time axis. Regulated heating of such catalysts allows the catalyst function to be regulated to a certain extent, but is impossible when using gas sensors having a sensitive reaction to gas compositions and fluctuations in gas compositions. This is because very high catalyst temperatures are employed almost exclusively so that considerable changes are brought about in the measurement gas due to thermal induction of chemical processes. Consequently, such catalysts cannot be used in sensitive gas sensors as a rule. Also, for the most part, catalysts are not available for every gas component to be measured. Apart from a purposeful oxidation of the measurement gas, there remains the critical problem of the reactivity of the measurement gas with the measurement electrode.

Solid electrolyte sensors often have cross-sensitivity to gases with high absorption at the measuring electrode. For example, chlorine sensors exhibit a substantial cross-sensitivity to hydrogen sulfide because the sulfur split off from the hydrogen sulfide coats the measurement electrode of the solid electrolyte sensor. Reductive gases such as hydrogen interfere with the measuring properties of solid electrolyte sensors, since these gases reduce the oxidic solid electrolyte and accordingly permanently change its material characteristics. Naturally, in time, this not only leads to a reduction in measuring accuracy, but also to the destruction of the sensor.

When measurement gas components and ions of the solid electrolyte form oxidic compounds, the electromotive force generated by the sensor also depends on the concentration of oxygen. This means that a knowledge of the oxygen concentration is necessary for determining the concentration of the measurement gas component. An additional oxygen sensor is accordingly required. This is a disadvantage in DE-OS 36 33740, in which precisely such an oxygen sensor is necessary.

SUMMARY OF THE INVENTION

Accordingly, it is an object of the present invention to provide a solid electrolyte sensor device in which the disruptive adsorption of measurement gas components on the sensor or on the corresponding sensor electrode is permanently prevented.

Pursuant to this object, and others which will become apparent hereafter, one aspect of the present invention resides in a solid electrolyte sensor device in which an adjustable oxygen source is arranged in the vicinity of the sensor electrode facing a measurement space containing the measurement gas and oxygen or oxygen radicals may be introduced into the measurement gas via this oxygen source.

The advantages of the present invention over the prior art discussed above are considerable. Destructive chemical corrosion and adsorption on the sensor electrode is prevented by the invention in that the oxidation of the measurement gas and the measurement gas component or components is spatially limited to the sensor. Even if the sensor electrode is relatively stable chemically against such chemical influences, the adsorption of chemical elements on the sensor electrode is prevented and the measurement accuracy is accordingly retained. For this purpose, the ability to regulate the oxygen source which introduces the oxygen or oxygen radicals into the measurement gas in a determined location is essential. In contrast to the use of surface catalysts for oxidation, the degree of oxidation of the measurement gas can always be optimized and does not change over time. Accordingly, accuracy of measurement is permanently maintained in the present invention.

In a further advantageous embodiment of the invention, the electrical means for detecting and processing sensor output contains a regulating device which regulates the amount of oxygen introduced from the oxygen source for the oxidation of the measurement gas as a function of the electromotive force developed by the sensor element and depending on the concentration of measurement gas. Thus, the electrical output value of the sensor is advisably regeneratively coupled with an optimal adjustment of the oxygen addition.

In another embodiment, the measurement gap or measurement space and the maximum adjustable oxygen addition of the oxygen source are advisably adapted to one another in terms of dimensions so that the given flow of measurement gas through the measurement gap in the case of the application in question is less than or equal to the maximum adjustable "inflowing" flow of oxygen. In so doing, the dimensioning of the measurement gap also takes into account the sensor surface or electrode surface required for a suitably sensitive measurement. Further, the possible or maximum possible rate of flow enabled by the measurement gap geometry in connection with the reactivity of the electrode or sensor is also taken into account. That is, at a correspondingly high flow of measurement gas, the oxygen source must be dimensioned so as always to ensure that all of the molecules to be oxidized can indeed be oxidized. In this way, a guideline is provided for the dimensioning of the sensor device required for ensuring the aimed for optimum operation in each specific case.

Further advantageous embodiments are directed to the oxygen source as such, which can also be regulated by way of the construction of the solid electrolyte. In this way, the entire device can be regulated in a simple manner. Still a further embodiment concerns the accurate positioning of flow-in openings so that either the flow is effected diametrically through the measurement gap along its longitudinal extension or, e.g., the opening is constructed through the oxygen source in a special closed off construction of the measurement space. In this connection, in this embodiment the electrode of the oxygen source facing the measurement gap or measurement space also at least partially extends into the opening on the inner surface of the opening. In so doing, the introduced measurement gas is oxidized already on its way into the measurement space, i.e. before reaching the measurement space. It should be noted by way of explanation that the measurement gas is introduced into the sensor by diffusion based on a concentration gradient, rather than in a flow in the classic sense. This is true for all embodiments for the introduction of the measurement gas which thus "diffuses into" the sensor. This is a diffusion since the dimensions of the sensor and gap are correspondingly small. Accordingly, the flow-in openings or slits for the measurement gas are to be viewed rather as diffusion openings.

The various features of novelty which characterize the invention are pointed out with particularity in the claims annexed to and forming a part of the disclosure. For a better understanding of the invention, its operating advantages, and specific object attained by its use, reference should be had to the drawing and descriptive matter in which there are illustrated and described preferred embodiments of the invention.

DETAILED DESCRIPTION OF THE PREFERRED EMBODIMENTS

Figure 1A:
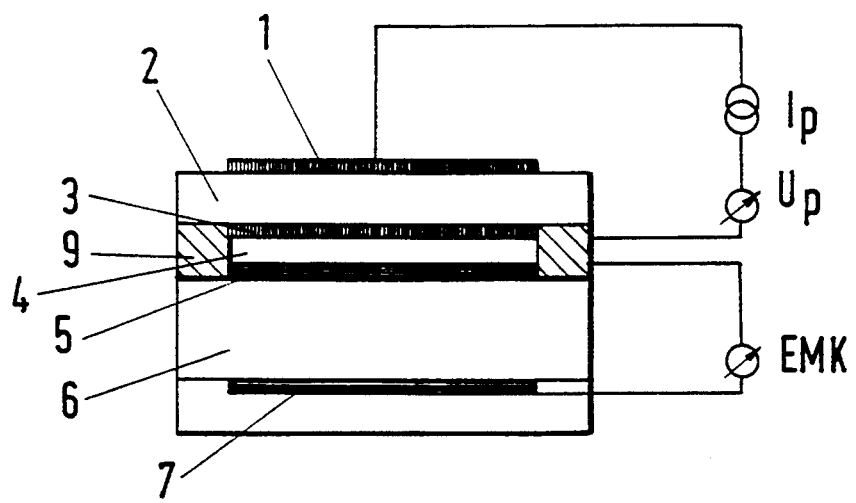
FIGS. 1a and 1b show a solid electrolyte sensor device pursuant to the present invention in which flow is effected diametrically through the measurement gap.

A section through the sensor device is shown in FIG. 1a. The actual sensor is formed by a solid electrolyte 6 and the two electrodes 5 and 7. The electrode 5 faces the measurement space 4 containing the measurement gas. The oxygen source 2 which is provided with electrodes 1 and 3 is arranged above spacers 9. A solid electrolyte which is provided at either side with the electrodes 1 and 3, respectively, is used in this oxygen source 2. The electrode 3 likewise faces the measurement space 4. This means that electrodes 3 and 5 substantially define the measurement space 4. The electrodes 1, 3 and 5, 7 are porous or permeable to gas. When electrical voltage is applied to the electrodes 1, 3 and accordingly flows through the solid electrolyte 2 of the pump current IP, the oxygen source releases a definable amount of oxygen into the measurement space 4 for oxidizing the measurement gas. As a result, optimum oxidation of the measurement gas, which may be aggressive, can always be carried out in a regulated manner so that the electrode 5 of the actual sensor is no longer exposed to the chemical attack of a reactive measurement gas.

Figure 1B:
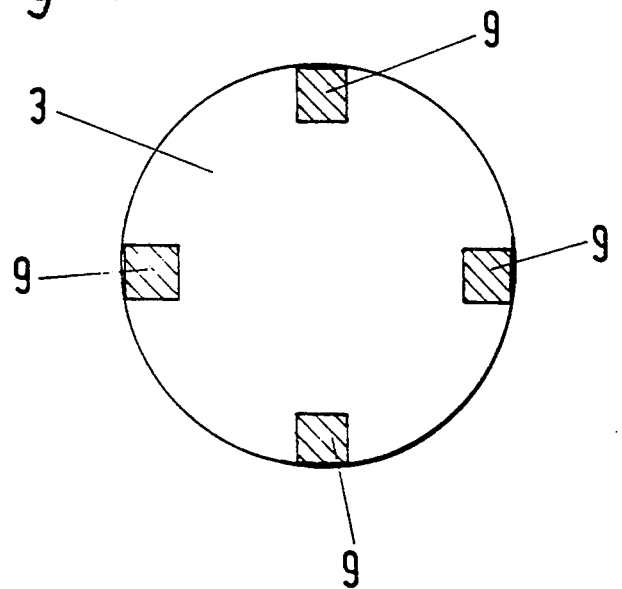

FIG. 1b shows the oxygen source as seen directly facing the electrode surface 3. It will be seen that the spacers 9 do not extend annularly, but are provided only as spacer elements between which abundant space is provided so that the measurement gas can diffuse into the measurement space.

Figure 2:
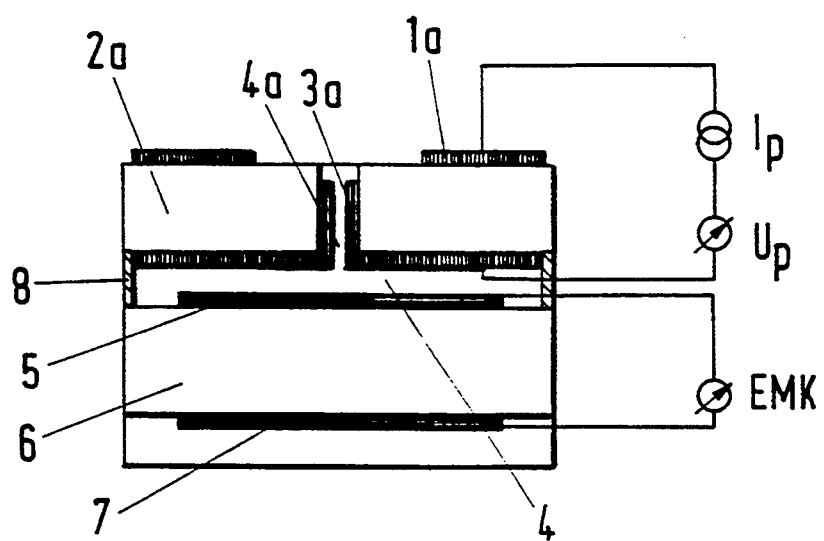
FIG. 2 shows the solid electrolyte sensor device with a closed measurement space and an inlet opening through the oxygen source.

FIG. 2 shows an embodiment in which the sensor device encloses the measurement space 4 with a wall 8 and in which the diffusion of the measurement gas is effected via a diffusion hole 4a made through the oxygen source. The above statements relating to the diffusion are clearly illustrated in this figure. In this case, there is no flow through the measurement space; rather the measurement gas diffuses in through the diffusion hole 4a based on a concentration gradient. The electrodes 1a, 3a of the oxygen source 2a are constructed in such a way that the outer electrode 1a is arranged circumferentially around the diffusion hole and the inner electrode 3a facing the measurement gap extends over the surface of the measurement space and, at the same time, reaches into the diffusion hole 4a and covers the inner wall of the diffusion hole at least partially. This results in the advantage, already mentioned above, that the measurement gas can be oxidized already in the course of entering through the diffusion hole 4a before reaching the measurement space. The electrodes mentioned above are naturally also porous, i.e. permeable to gas.

Figure 3A:
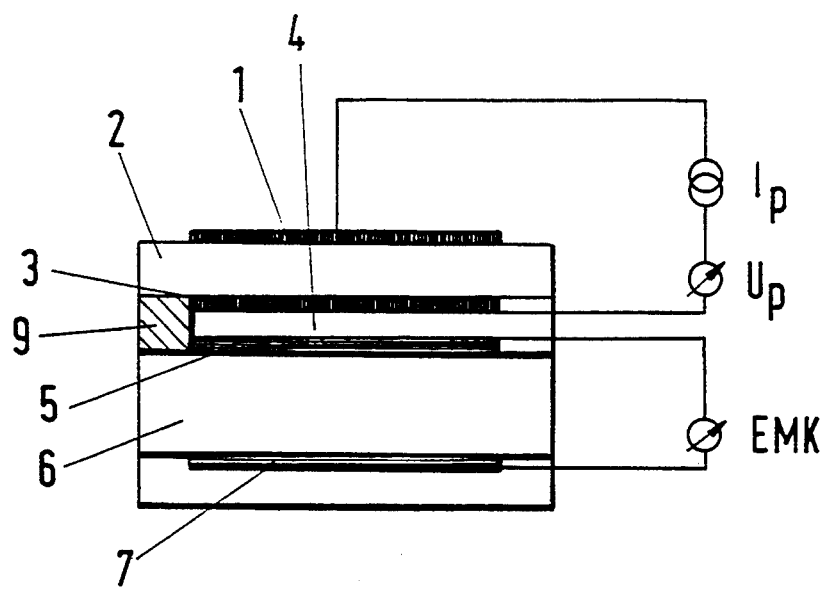
FIGS. 3a and 3b show the solid electrolyte sensor device with an inlet opening arranged in the edge area of the measurement gap.
Figure 3B:
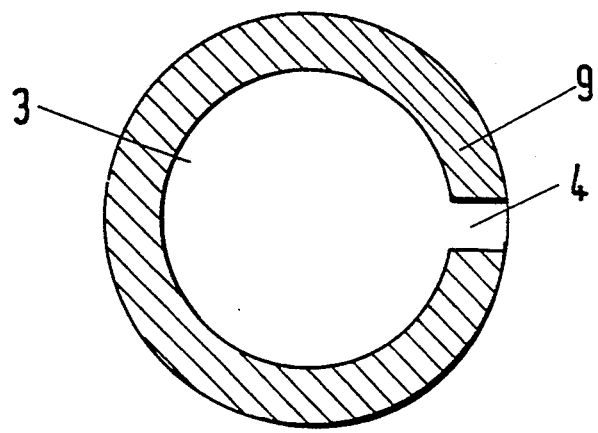

FIGS. 3a and 3b show the sensor device with a lateral inlet opening. An opening arranged in the region of the spacer 9 can be seen in FIG. 3a at the side. In a corresponding view as seen from the measurement space, FIG. 3b shows that the spacer 9 does not form a closed circle, but rather leaves a corresponding opening which opens into the measurement gap 4. This figure also clearly shows that there is no flow in the classic sense, but that the measurement gas diffuses into the measurement space from the outside based on the concentration.

Figure 4:
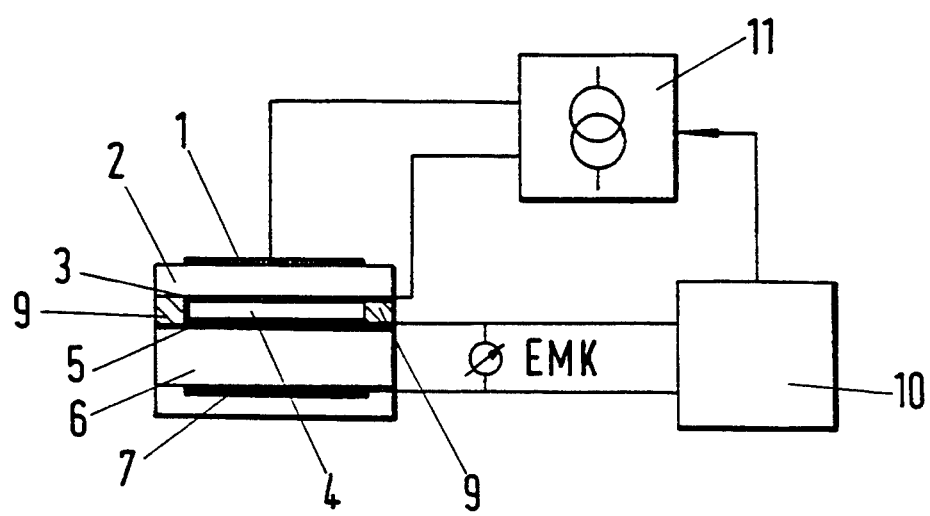
FIG. 4 shows the sensor with the external electrical circuitry.

FIG. 4 shows the external circuitry. Depending on the concentration of the measurement gas, there is a corresponding emf (electromotive force) between the electrodes 5 and 7 of the actual sensor. This emf is detected and supplied to a regulating device 10. The output of the regulating device 10 is connected to a current source 11 which regulates the current through the oxygen source. In so doing, the current flows via the solid electrolyte 2 of the oxygen source and via the electrodes 1 and 3. As a result of the appropriate action on the part of the regulating device 10 upon the current source, it is possible for the oxygen requirement in the measurement space 4 to be continually adjusted corresponding to the emf value depending on the concentration of measurement gas so that an optimal oxidation of the measurement gas or measurement gas component to be oxidized can always be achieved.

The invention is not limited by the embodiments described above which are presented as examples only but can be modified in various ways within the scope of protection defined by the appended patent claims.

I claim:

1. A solid electrolyte sensor device for determining gas concentrations in measurement gas, comprising: a sensor formed by a solid electrolyte which is arranged between at least two *gas permeable* electrodes, the sensor producing output values; electrical means for detecting and processing concentration-dependent sensor output values; an adjustable oxygen source arranged at a distance from one of the sensor electrodes so that the oxygen source and the one sensor electrode face one another and the measurement gas, whereby one of oxygen and oxygen radicals are introduced into the measurement gas for oxidation of the measurement gas; and at least one spacer which holds the oxygen source and the sensor electrode at a distance from one another to form a measurement space which is closed except for at least one through-opening, a volume of the measurement space and a maximum adjustable amount of oxygen introduced from the oxygen source into the measurement gas are dimensioned so that a maximum measurement gas flow in a given application is no more than the maximum adjustable amount of oxygen introduced from the oxygen source.

2. A solid electrolyte sensor device according to claim 1, wherein the electrical means include a regulating device which regulates the amount of oxygen introduced from the oxygen source for oxidizing the measurement gas as a function of electromotive force which is formed by the sensor and depends on the concentration of measurement gas.

3. A solid electrolyte sensor device according to claim 1, wherein the oxygen source has an electrode corresponding to the sensor electrode, the sensor electrode facing the measurement gas and one of the oxygen source and the corresponding electrode of the oxygen source are located opposite one another to form a gap through which the measurement gas flows or is diffused.

4. A solid electrolyte sensor device according to claim 1, wherein the oxygen source is formed by a solid electrolyte which is arranged between at least two gas-permeable electrodes and at least one of the electrodes faces the measurement gas.

5. A solid electrolyte sensor device according to claim 4, wherein the spacer is constructed as a wall which completely encloses the measurement space, the through-opening into the measurement space is through the oxygen source, the electrode of the oxygen source which faces the measurement space extends into the opening at least partially on an inner surface of the opening.

6. A solid electrolyte sensor device according to claim 5, wherein the electrode of the oxygen source remote of the measurement space extends annularly around the opening.

7. A solid electrolyte sensor device according to claim 1, wherein one of the openings to the measurement space and the measurement gap are provided so that at least two openings lie diametrically opposite one another with reference to edges of one of the measurement gap and the measurement space so that measurement gas can flow through the measurement gap longitudinally.

* * * * *